United States Patent
Shaw et al.

(10) Patent No.: US 10,436,800 B2
(45) Date of Patent: Oct. 8, 2019

(54) 13+/17+ BIN1 EXPRESSION AS A MARKER OF CARDIAC DISORDERS

(71) Applicant: Sarcotein Diagnostics, LLC, Tampa, FL (US)

(72) Inventors: Darryl Steven Shaw, Tampa, FL (US); Neil Gavin Shaw, Tampa, FL (US)

(73) Assignee: SARCOTEIN DIAGNOSTICS, LLC, Tampa, FL (US)

( * ) Notice: Subject to any disclaimer, the term of this patent is extended or adjusted under 35 U.S.C. 154(b) by 0 days.

(21) Appl. No.: 15/555,043

(22) PCT Filed: Mar. 2, 2016

(86) PCT No.: PCT/US2016/020495
§ 371 (c)(1),
(2) Date: Aug. 31, 2017

(87) PCT Pub. No.: WO2016/141088
PCT Pub. Date: Sep. 9, 2016

(65) Prior Publication Data
US 2018/0038874 A1 Feb. 8, 2018

Related U.S. Application Data

(60) Provisional application No. 62/126,867, filed on Mar. 2, 2015.

(51) Int. Cl.
| | | |
|---|---|---|
| G01N 33/68 | (2006.01) | |
| C07K 14/47 | (2006.01) | |
| C07K 16/18 | (2006.01) | |

(52) U.S. Cl.
CPC ..... *G01N 33/6893* (2013.01); *C07K 14/4703* (2013.01); *C07K 14/4747* (2013.01); *C07K 16/18* (2013.01); *C07K 2317/565* (2013.01); *G01N 2333/47* (2013.01); *G01N 2800/32* (2013.01); *G01N 2800/325* (2013.01); *G01N 2800/326* (2013.01); *G01N 2800/50* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 4,342,566 | A | 8/1982 | Theofilopoulos et al. |
| 6,048,702 | A | 4/2000 | Prendergast et al. |
| 6,410,238 | B1 | 6/2002 | Prendergast et al. |
| 6,461,828 | B1 | 10/2002 | Stanton et al. |
| 6,831,063 | B1 | 12/2004 | Prendergast et al. |
| 7,150,968 | B2 | 12/2006 | Prendergast et al. |
| RE39,816 | E | 9/2007 | Stanton et al. |
| 8,999,659 | B2 * | 4/2015 | Shaw ............... G01N 33/6893 435/7.92 |
| 9,150,924 | B2 | 10/2015 | Shaw et al. |
| 9,846,159 | B2 | 12/2017 | Shaw et al. |
| 9,891,232 | B2 | 2/2018 | Shaw et al. |
| 2003/0166021 | A1 | 9/2003 | Prendergast et al. |
| 2004/0106954 | A1 | 6/2004 | Whitehurst et al. |
| 2004/0241764 | A1 | 12/2004 | Galili |
| 2005/0064455 | A1 | 3/2005 | Baker et al. |
| 2005/0260697 | A1 | 11/2005 | Wang et al. |
| 2006/0003959 | A1 | 1/2006 | Burden et al. |
| 2006/0263813 | A1 | 11/2006 | Rosenberg et al. |
| 2009/0088482 | A1 | 4/2009 | Maybaum et al. |
| 2010/0086481 | A1 | 4/2010 | Baird et al. |
| 2010/0092983 | A1 | 4/2010 | Liew |
| 2011/0008346 | A1 | 1/2011 | Duckers |
| 2011/0217713 | A1 | 9/2011 | Weaver et al. |
| 2012/0094300 | A1 | 4/2012 | Shaw et al. |
| 2013/0266975 | A1 | 10/2013 | Shaw et al. |
| 2013/0324432 | A1 | 12/2013 | Shaw et al. |
| 2015/0233947 | A1 | 8/2015 | Shaw et al. |
| 2018/0172693 | A1 | 6/2018 | Shaw et al. |

FOREIGN PATENT DOCUMENTS

| | | | |
|---|---|---|---|
| WO | WO-94/29348 | | 12/1994 |
| WO | WO-98/55151 A1 | | 12/1998 |
| WO | WO-01/04354 A2 | | 1/2001 |
| WO | WO-2007/130549 | | 11/2007 |
| WO | WO-2010/124240 A2 | | 10/2010 |
| WO | WO2012/054764 A1 | | 4/2012 |
| WO | WO-2012/087437 | | 6/2012 |
| WO | WO2013/049666 A1 | | 4/2013 |
| WO | WO-2013049666 A1 * | 4/2013 | ....... G01N 33/57419 |

OTHER PUBLICATIONS

Lloyd et al. Protein Engineering, Design & Selection 2009, 22:159-168 (Year: 2009).*
Edwards et al., J Mol Biol. Nov. 14, 2003;334(1):103-118 (Year: 2003).*
Ward (Nature 341:544-546 (1989) (Year: 1989).*
Casset et al. ((2003) BBRC 307, 198-205 (Year: 2003).*
De Pascalis et al. The Journal of Immunology (2002) 169, 3076-3084 (Year: 2002).*
Padlan et al. (PNAS 1989, 86:5938-5942) (Year: 1989).*
Lamminmaki et al. (J BC 2001,276:36687-36694) (Year: 2001).*
U.S. Appl. No. 15/827,568, filed Nov. 30, 2017, Shaw et al.
Chang et al., "BIN1 (bridging integrator 1)," Atlas Genet Cytogenet Oncol Haematol., (2009), 13(8):543-548.
Fernando et al., "Bin 1 Src Homology 3 Domain Acts as a Scaffold for Myofiber Sarcomere Assembly," J. of Biological Chemistry, (2009), 284(40):27674-27686.
Muller, "Marrying Immunotherapy with Chemotherapy: Why Say IDO?", Cancer Research, vol. 65, No. 18, (Sep. 15, 2005), pp. 8065-868.

(Continued)

*Primary Examiner* — Daniel C Gamett
(74) *Attorney, Agent, or Firm* — Foley & Lardner LLP (57) ABSTRACT

Provided are methods of determining if a subject has a cardiac disorder or is at risk for developing a cardiac disorder.

18 Claims, 2 Drawing Sheets

Specification includes a Sequence Listing.

(56) References Cited

OTHER PUBLICATIONS

Nicot et al., "Mutations in amphiphysin 2 (BIN1)disrupt interaction with dynamin 2 and cause autosomal recessive centronuclear myopathy," Nat. Genet., (2007), 39(9):1134-1139.
PCT International Preliminary Report on Patentability (Chapter 1) for Application No. PCT/US2016/020495 dated Sep. 14, 2017. (7 pages).
Tajiri et al., "Expression of a MYCN-interacting Isoform of the Tumor Suppressor BIN1 is Reduced in Neuroblastomas with Unfavorable Biological Features", Clinical Cancer Research, (Sep. 5, 2013), pp. 3345-3355.
Toussaint et al., "Defects in Amphiphysin 2 (BIN1) and Triads in Several Forms of Centronuclear Myopathies," Acta. Neuropathol., (2011), 121(2):253-266.
U.S. Office Action for U.S. Appl. No. 13/884,454 dated Dec. 23, 2016. (19 pages).
U.S. Office Action for U.S. Appl. No. 13/884,454 dated Jun. 15, 2017. (20 pages).
U.S. Notice of Allowance for U.S. Appl. No. 13/884,454 dated Oct. 4, 2017. (17 pages).
U.S. Office Action for U.S. Appl. No. 14/348,269 dated Feb. 12, 2016. (15 pages).
U.S. Office Action for U.S. Appl. No. 14/348,269 dated Sep. 22, 2016. (17 pages).
U.S. Office Action for U.S. Appl. No. 14/348,269 dated Mar. 8, 2017. (12 pages).
U.S. Notice of Allowance for U.S. Appl. No. 14/348,269 dated Aug. 16, 2017. (5 pages).
Wechsler-Reya et al., "A Role for the Putative Tumor Suppressor Bin1 in Muscle Cell Differentiation," Molecular and Cellular Biology, (1998), 18(1):566-575.
*Ariosa Diagnostics, Inc. v. Sequenom, Inc.*, Opinion of the US Court of Appeals for the Federal Circuit, Jan. 21, 2015.
Barth, et al. (2002) "Dissecting interactions between EB1, microtubules and APC in cortical clusters at the plasma membrane" J. Cell Sci. 115(Pt. 8): 1583-1590.
Basso et al. (2009) "Arrhythmogenic right ventricular cardiomyopathy" Lancet 373(9671): 1289-1300.
Bers (2002) "Cardiac excitation-contraction coupling" Nature 415(6868): 198-205.
Beuckelmann et al., "Intracellular calcium handling in isolated ventricular myocytes from patients with terminal heart failure", Circulation, Mar. 1992; 85(3):1046-55.
Birks et al., "Left ventricular assist device and drug therapy for the reversal of heart failure", N Engl J Med., 2006, 355(18):1873-84.
Blaxall et al., "Differential gene expression and genomic patient stratification following left ventricular assist device support", J Am Coll Cardiol., Apr. 2, 2003;41(7):1096-1106.
Bodor et al. (1997) "Troponin I Phosphorylation in the Normal and Failing Adult Human Heart" Circulation 96(5):1495-1500.
Brette & Orchard (2007) "Resurgence of Cardiac T-Tubule Research" Physiology (Bethesda) 22:167-173.
Butler, et al. (1997) "Amphiphysin II (SH3P9; BIN1), a member of the amphiphysin/Rvs family, is concentrated in the cortical cytomatrix of axon initial segments and nodes of ranvier in brain and around T tubules in skeletal muscle", J. Cell Biol. 137(6):1355-1367.
Casset et al., "A peptide mimetic of an anti-CD4 monoclonal antibody by rational design", Biochemical and Biophysical Research Communications, 2003, vol. 307, pp. 198-205.
Chang, et al. (2007) Bin1 Ablation in Mammary Gland Delays Tissue Remodeling and Drives Cancer Progression. Cancer Res. 67(1):100-107.
Chang, et al. (2007) Bin1 Ablation Increases Susceptibility to Cancer during Aging, Particularly Lung Cancer. Cancer Res. 67(16):7605-7612.
Chen, et al. (2002) "L-type Ca2+ channel density and regulation are altered in failing human ventricular myocytes and recover after support with mechanical assist devices" Circ. Res. 91(6):517-524.

Cheng, et al. (1993) "Calcium sparks: elementary events underlying excitation-contraction coupling in heart muscle" Science 262(5134):740-744.
Dalzell et al., "Novel biomarkers in heart failure: An overview", Biomarkers in Medicine, Future Medicine, London, 2009, 3(5):453-463.
De Groote et al., "The impact of beta-adrenoreceptor genepolymorphisms on survival in patients with congestive heart failure", Eur J Heart Fail, (2005), vol. 7, No. 6, p. 966-973.
Dipla, et al. (1998) "Myocyte recovery after mechanical circulatory support in humans with end-stage heart failure" Circulation 97:2316-2322.
Doust et al., "How well does B-type natriuretic peptide predict death and cardiac events in patients with heart failure: systematic review", BMJ, 2005, 330(7492):625. Review.
Etienne-Manneville & Hall (2003) "Cdc42 regulates GSK-3~ and adenomatous polyposis coli to control cell polarity" Nature 421(6924):753-756.
Fabiato (1983) "Calcium-induced release of calcium from the cardiac sarcoplasmic reticulum" Am. J. Physiol. 245(I):CI-C14.
Ge et al., "Mechanism for elimination of a tumor suppressor: Aberrant splicing of a brain-specific exon causes loss of function of Bin1 in melanoma," Proc. Natl. Acad. Sci. USA, Aug. 1999, 96(17): 9689-9694.
Gomez, et al. (1997) "Defective excitation-contraction coupling in experimental cardiac hypertrophy and heart failure" Science 276(5313):800-806.
Green, et al. (2005) "APC and EB1 function together in mitosis to regulate spindle dynamics and chromosome alignment" Mal. Biol. Cell 16(10):4609-4622.
Gwathmey, et al. (1987) "Abnormal intracellular calcium handling in myocardium from patients with end-stage heart failure" Circ. Res. 61(1):70-76.
Hama et al. (1995) "Rapid Ventricular Induction of Brain Natriuretic Peptide Gene Expression in Experimental Acute Myocardial Infarction" Circulation 92(6):1558-1564.
Harding, et al. (1994) "Contractile function and response to agonists in myocytes from failing human heart" Eur. Heart J. 15(Suppl. D):35-36.
Hasenfuss, et al. (1999) "Relationship between Na+-Ca2+-exchanger protein levels and diastolic function of failing human myocardium" Circulation 99(5):641-648.
Hasenfuss, G., "Alterations of calcium-regulatory proteins in heart failure", Cardiovasc Res., 1998, 37(2):279-89. Review.
Hesse et al., "Dilated cardiomyopathy is associated with reduced expression of the cardiac sodium channel Scn5a", Cardiovasc Res., (2007), vol. 75, No. 3, p. 498-509.
Holm et al., "Functional mapping and single chain construction of the anti-cytokeratin 8 monoclonal antibody TS1", Molecular Immunology, 2007, vol. 44, pp. 1075-1084.
Hong et al. (2012) "Plasma BIN1 correlates with heart failure and predicts arrhythmia in patients with arrhythmogenic right ventricular cardiomyopathy" Heart Rhythm, 9(6):961-970.
Hong et al., "BIN1 localizes the L-type calcium channel to cardiac T-tubules", PLOS Biol., (Feb. 16, 2010), vol. 8, No. 2, pp. E1000312-1-E1000312-14.
Horwitz et al., "Detection of cardiac allograft rejection and response to immunosuppressive therapy with peripheral blood gene expression", Circulation, 2004, 110(25):3815-21.
Huang et al. (1999) "Cardiac troponin I gene knockout: a mouse model of myocardial troponin I deficiency" Circ Res 84(1):1-8.
Hullin, et al. (1999) "Subunit expression of the cardiac L-type calcium channel is differentially regulated in diastolic heart failure of the cardiac allograft" Circulation 100(2):155-163.
Hulot et al. (2004) "Natural history and risk stratification of arrhythmogenic right ventricular dysplasia/cardiomyopathy" Circulation 110(14): 1879-1884.
Hunkeler et al. (1991) "Troponin I isoform expression in human heart" Circ Res 69(5):1409-1414.
Inui, et al. (1987) "Isolation of the ryanodine receptor from cardiac sarcoplasmic reticulum and identity with the feet structures" J. Biol. Chem. 262(32):15637-15642.

(56) References Cited

OTHER PUBLICATIONS

Karni et al., "The gene encoding the splicing factor SF2/ASF is a proto-oncogene," Nature Structural & Molecular Biology, vol. 14, No. 3, Mar. 2007, pp. 185-193.
Labaer et al., "So, You Want to Look for Biomarkers (Introduction to the Special Biomarkers Issue", Journal of Proteome Research, 2005, vol. 4(4), pp. 1053-1059.
Lee et al., "Amphiphysin 2 (Bin1) and T-tubule biogenesis in muscle", Science, (2002) 297: 1193-1196.
Lehnart, et al. (2005) "Phosphodiesterase 4D deficiency in the ryanodine-receptor complex promotes heart failure and arrhythmias" Cell 123(1):25-35.
Ligon & Holzbaur (2007) "Microtubules tethered at epithelial cell junctions by dynein facilitate efficient junction assembly" Traffic 8(7):808-819.
LIMR Link The Newsletter of the Lankenau Institute for Medical Research, Summer 2008. www.lirnr.org.
Litwin, et al. (2000) "Dyssynchronous Ca(2+) sparks in myocytes from infarcted hearts" Circ. Res. 87(11):1040-1047.
Lonberg et al., "Human Antibodies from Transgenic Mice," Intern. Rev. Immunol., vol. 13, 1995, pp. 65-93.
Lukaski, H., "Sarcopenia: Assessment of Muscle Mass", American Society for Nutritional Sciences, 1997, 127:994S-997S.
MacCallum et al., "Antibody-antigen Interactions: Contact Analysis and Binding Site Topography", J. Mol. Biol., 262:732-745, Oct. 1996.
Maeda et al., "High levels of plasma brain natriuretic peptide and interleukin-6 after optimized treatment for heart failure are independent risk factors for morbidity and mortality in patients with congestive heart failure", J Am Coll Cardiol., 2000, 36(5):1587-1593.
Marcus et al. (2010) "Diagnosis of arrhythmogenic right ventricular cardiomyopathy/dysplasia: proposed modification of the task force criteria" Circulation 121:1533-1541.
Marx, et al. (2000) "PKA phosphorylation dissociates FKBP12.6 from the calcium release channel (ryanodine receptor): defective regulation in failing hearts" Cell 101(4):365-376.
Mayeux et al., "Biomarkers: Potential uses and Limitations", NeuroRx, 2004, vol. 1, pp. 182-188.
McKenna, Circulation, 1996; 93: 841-842, Report of the 1995 World Health Organization/International Society and Federation of Cardiology Task Force on the Definition and Classification of Cardiomyopathies, whole article).
Mewes & Ravens (1994) "L-type calcium currents of human myocytes from ventricle of nonfailing and failing hearts and from atrium" J. Mal. Cell. Cardiol. 26(10):1307-1320.
Missov et al. (1997) "Circulating cardiac troponin I in severe congestive heart failure" Circulation 96(9):2953-2958.
Mukherjee et al., "Changes in L-type calcium channel abundance and function during the transition to pacing-induced congestive heart failure", Cardiovasc Res., 1998, 37(2):432-444.
Muller et al., "Inhibition of indoleamine 2,3-dioxygenase, an immunoregulatory target of the cancer suppression gene Bin1, potentiates cancer chemotherapy," Nature Medicine, Mar. 2005, 11(3): 312-319.
Muller et al., "Targeted disruption of the murine Bin1/Amphiphysin II gene does not disable endocytosis but results in embryonic cardiomyopathy with aberrant myofibril formation", Mol Cell Biol, (2003) 23: 4295-4306.
MyBioSource.com, "Anti-BIN1 Antibody:: Rabbit BIN1 Polyclonal Antibody", 2006, 1-4.
NCBI GenBank Accession No. NM_004305, Nov. 1, 2000.
Neufeld & White (1997) "Nuclear and cytoplasmic localizations of the adenomatous polyposis coli protein" Proc. Natl. Acad. Sci. U.S.A. 94(7):3034-3039.
Novitskiy et al., "Turn Off the IDO: Will Clinical Trials Be Successful?," Cancer Discovery, Aug. 2012, 2(8): 673-675.
Pascalis et al., "Grafting of "Abbreviated" complementarity-determining regions containing specificity-determining residues essential for ligand contact to engineer a less immunogenic humanized monoclonal antibody", Journal of Immunology, 2002, vol. 169, pp. 3076-3084.
Paul, "Fundamental Immunology", 3rd Edition, 1993, pp. 292-295.
PCT Search Report and Written Opinion for Application No. PCT/US2010/032282 dated Jan. 24, 2011. (7 pages).
PCT Search Report and Written Opinion for Application No. PCT/US2011/057155 dated Mar. 2, 2012. (6 pages).
PCT Search Report and Written Opinion for Application No. PCT/US2011/059574 dated Jun. 20, 2012. (12 pages).
PCT Search Report and Written Opinion for Application No. PCT/US2012/058051 dated Jan. 28, 2013. (18 pages).
PCT Preliminary Report on Patentability (Chapter 1) for Application No. PCT/US2010/032282 dated Nov. 3, 2011. (5 pages).
PCT Preliminary Report on Patentability (Chapter 1) for Application No. PCT/US2011/057155 dated Apr. 23, 2013. (5 pages).
PCT Preliminary Report on Patentability (Chapter 1) for Application No. PCT/US2011/059574 dated May 14, 2013. (7 pages).
PCT Preliminary Report on Patentability (Chapter 1) for Application No. PCT/US2012/058051 dated Apr. 1, 2014. (10 pages).
Pessah, et al. (1985) "The calcium-ryanodine receptor complex of skeletal and cardiac muscle" Biochem. Biophys. Res. Commun. 128(1):449-456.
Pineda-Lucena et al., "A Structure-based Model of the c-Myc/Bin1 Protein Interaction Shows Alternative Splicing of Bin1 and c-Myc Phosphorylation are Key Binding Determinants," J. Mol. Biol. (2005) 351, pp. 182-194.
Piot et al., "High frequency-induced up regulation of human cardiac calcium currents", Circulation, 1996, 93(1):120-8.
Pollack, A., "Doctors Seek Way to Treat Muscle Loss", The New York Times, Aug. 30, 2010; retrieved at http://www.nytimes.com/2010/08/31/health/research/31muscle.html.
Pollack, et al. (1997) "Dynamics ofbeta-catenin interactions with APC protein regulate epithelial tubulogenesis" J. Cell Biol. 137(7):1651-1662.
Prendergast et al., "BAR the door: cancer suppression by amphiphysin-like genes," Biochim Biophys Acta., Jan. 2009, 1795(1): 25-36.
Radpour et al., "Hypermethylation of Tumor Suppressor Genes Involved in Critical Regulatory Pathways for Developing a Blood-Based Test in Breast Cancer," PLoS One 6(1): e16080, Jan. 2011, 11 pages.
Ricchiuti et al. (1997) "Cardiac troponin I and T alterations in hearts with severe left ventricular remodeling" Clin Chem 43(6):990-995.
Roy et al., "Evidence that public database records for many cancer-associated genes reflect a splice form found in tumors and lack normal splice forms", Nucl Acid Res, 2005; 33:5026-5032.
Rudikoff et al., "Single amino acid substitution altering antigen-binding specificity", Proc. Natl. Acad. Sci. USA, 79(6):1979-1983, Mar. 1982.
Schneider, "Tumor markers in detection of lung cancer", Adv Clin Chem, 2006; 42:1-41.
Schroder et al., "Increased availability and open probability of single L-type calcium channels from failing compared with nonfailing human ventricle", Circulation, 1998, 98(10):969-976.
Scriven, et al. (2000) "Distribution of proteins implicated in excitation-contraction coupling in rat ventricular myocytes" Biophys. J. 79(5):2682-2691.
Sedwick C., "BIN1: a protein with great heart", PLOS Biol., (20100216), vol. 8, No. 2, pp. E1000311-1-E1000311-2.
Sen-Chowdhry et al. (2005) "Genetics of right ventricular cardiomyopathy" J Cardiovasc Electrophysiol 16(8):927-935.
Shaw, et al. (2007) "Microtubule plus-end-tracking proteins target gap junctions directly from the cell interior to adherens junctions" Cell 128(3):547-560.
Siew et al., "Biological Markers of Acute Kidney Injury", J Am Soc Nephrol, 22:810-820, 2011.
Sigma Clone 99 Antibody (1999, Product information retrieved from URL:www.sigmaaldrich.com/catalog/product/sigma/b9428?lang=en?ion=US.
Sipido, et al. (1998) "Frequency dependence of Ca2+ release from the sarcoplasmic reticulum in human ventricular myocytes from end-stage heart failure" Cardiovasc. Res. 37(2):478-488.

(56) References Cited

OTHER PUBLICATIONS

Slomianka, L., "Blue Histology—Muscle", School of Anatomy and Human Biology, The University of Western Australia, 2009, 1-14.
Smith et al., "IDO Is a Nodal Pathogenic Driver of Lung Cancer and Metastasis Development," Cancer Discovery, Aug. 2012, 2(8): 722-735.
Stampfer et al., "Risk Factor Criteria", Circulation, 2004;109:IV-3-IV-5.
Takahashi, et al. (2004) "Membrane-associated guanylate kinase-like properties of betasubunits required for modulation of voltage-dependent Ca2+ channels" Proc. Natl. Acad. Sci. U.S.A. 101(18):7193-7198.
Tamura et al. (2000) "Cardiac fibrosis in mice lacking brain natriuretic peptide" Proc Natl Acad Sci USA 97(8):4239-4244.
Thomas et al., "Serum tumor markers: past, state of the art, and future", Int J Biol Markers, 2001; 16:73-86.
Tockman et al., "Considerations in bringing a cancer biomarker to clienical application", Cancer Res., 1992, 52:2711s-2718s.
U.S. Office Action for U.S. Appl. No. 13/265,531 dated Mar. 29, 2013. (28 pages).
U.S. Office Action for U.S. Appl. No. 13/265,531 dated Oct. 24, 2013. (11 pages).
U.S. Office Action for U.S. Appl. No. 13/884,454 dated Dec. 11, 2015. (22 pages).
U.S. Office Action for U.S. Appl. No. 13/884,454 dated Jun. 4, 2015. (19 pages).
U.S. Office Action for U.S. Appl. No. 14/176,985 dated Jan. 26, 2015. (12 pages).
U.S. Office Action for U.S. Appl. No. 14/176,985 dated May 12, 2015. (7 pages).
U.S. Office Action for U.S. Appl. No. 14/348,269 dated Jun. 6, 2015. (8 pages).
U.S. Office Action for U.S. Appl. No. 14/348,269 dated Oct. 7, 2015. (29 pages).
U.S. Office Action for U.S. Appl. No. 14/626,546 dated Feb. 27, 2017. (35 pages).
U.S. Office Action for U.S. Appl. No. 14/626,546 dated Oct. 23, 2017. (20 pages).
Wechsler-Reya et al., "Structural Analysis of the Human BIN1 Gene. Evidence for Tissue-Specific Transcriptional Regulation and Alternate RNA Splicing", The Journal of Biological Chemistry, 1997, 272(50):31453-31458.
Westfall & Solaro (1992) "Alterations in myofibrillar function and protein profiles after complete global ischemia in rat hearts" Circ Res 70(2):302-313.
Xu et al., "Discovery of novel splice forms and functional analysis of cancer-specific alternative splicing in human expressed sequences," Nucleic Acids Research, Oct. 2003, 31(19): 5635-5643.
Your Favorite Gene Search, Powered by Ingenuity, BIN1 Antibodies from Sigma, 1 page.
Hong et al., "Cardiac BIN1 Folds T-Tubule Membrane, Controlling Ion Flux and Limiting Arrhythmia", Nature Medicine, Jun. 2014, vol. 20, No. 6, pp. 624-632.
International Search Report for PCT/US2016/020495 dated Jun. 30, 2016.
Bing Xu. "The ESCRT-III pathway facilitates cardiomyocyte release of cB1N1-containing microparticles," PLOS Biology, pp. 1-28, Aug. 14, 2017.
Office Action dated Oct. 12, 2018 received in corresponding Canadian Patent Application No. 2,850,178, 4 pages.

* cited by examiner

13+/17+ BIN1 EXPRESSION AS A MARKER OF CARDIAC DISORDERS

CROSS-REFERENCE TO RELATED APPLICATIONS

This application claims the benefit of U.S. Provisional Application No. 62/126,867, filed Mar. 2, 2015 and International Application No. PCT/US2016/020495 filed Mar. 2, 2016, each of which is hereby incorporated herein by reference in its entirety.

BACKGROUND

Cardiac disorders are the leading cause of death in the United States. Therefore, methods for diagnosing cardiac disorders, methods for assessing the progression of cardiac disorders and methods for evaluating the efficacy of treatment for cardiac disorders are necessary.

SUMMARY

Provided are methods of determining if a subject has a cardiac disorder or is at risk for developing a cardiac disorder. The methods comprise contacting a biological sample from the subject with (i) an antibody that specifically binds to a polypeptide encoded by exon 13 of BIN1 (13+ BIN1 polypeptide) and (ii) an antibody that specifically binds to a polypeptide encoded by exon 17 of BIN1 (17+ BIN1 polypeptide), and determining a total level of 13+/17+ BIN1 polypeptide. In these methods, a decrease in the total 13+/17+ BIN1 polypeptide level as compared to a control level indicates that the subject has a cardiac disorder or is at risk for developing a cardiac disorder.

Also provided are methods of treating a subject for a cardiac disorder. The methods comprise determining if the subject has a cardiac disorder or is at risk for a cardiac disorder, by detecting a decrease in the level of 13+/17+ BIN1 polypeptide as compared to a control level in a sample from the subject, and treating the subject for the cardiac disorder.

Also provided are methods for determining the efficacy of a therapy for a cardiac disorder in a subject based on changes in the level of 13+/17+ BIN1 polypeptide in the subject. The methods can comprise contacting a first biological sample from the subject with (i) an antibody that specifically binds to 13+ BIN1 polypeptide and (ii) an antibody that specifically binds to a 17+ BIN1 polypeptide to determine a first 13+17+ BIN1 level, obtaining a second biological sample from the subject after at least one treatment with a first therapy for the cardiac disorder, contacting the second biological sample with (i) the antibody that specifically binds to 13+ BIN1 polypeptide and (ii) the antibody that specifically binds to a 17+ BIN1 polypeptide to determine a second 13+17+ BIN1 level, and comparing the first BIN1 polypeptide level with the second BIN1 polypeptide level. In these methods, if the BIN1 polypeptide level decreases or fails to increase in the second biological sample as compared to the first biological sample, a second therapy for the cardiac disorder can be selected for the subject. If the 13+17+ BIN1 level increases in the second sample as compared to the first sample, treatment of the subject with the first therapy for the cardiac disorder can be continued.

Further provided are methods for determining the progression of a cardiac disorder or an increase in the risk of developing a cardiac disorder in a subject. The methods can comprise obtaining a first biological sample from the subject, determining a first 13+17+ BIN1 polypeptide level in the first biological sample, obtaining a second biological sample from the subject, determining a second 13+17+ BIN1 polypeptide level in the second biological sample, and comparing the first 13+17+ BIN1 polypeptide level with the second 13+17+ BIN1 polypeptide level. In these methods, if the 13+17+ BIN1 polypeptide level decreases in the second biological sample as compared to the first biological sample, the cardiac disorder in the subject has progressed or the risk of developing a cardiac disorder has increased in the subject.

DESCRIPTION

Methods described herein are based on the finding that a subject can be diagnosed with a cardiac disorder or at risk for developing a cardiac disorder by detecting in a biological sample from the subject decreased levels of 13+/17+ BIN1 polypeptide. Therefore, provided herein are methods for determining if a subject has a cardiac disorder or is at risk for developing a cardiac disorder. The methods comprise contacting a biological sample from the subject with (i) an antibody that specifically binds to a polypeptide encoded by exon 13 of BIN1 (13+ BIN1 polypeptide) and (ii) an antibody that specifically binds to a polypeptide encoded by exon 17 of BIN1 (17+ BIN1 polypeptide) under conditions that allow identification of a 13+/17+ BIN1 polypeptide, wherein the 13+/17+ BIN1 polypeptide comprises the polypeptide encoded by exon 13 and the polypeptide encoded by exon 17; and determining a total level of 13+/17+ BIN1 polypeptide, wherein a decrease in the total level of 13+/17+ BIN1 polypeptide, as compared to a control level, indicates that the subject has a cardiac disorder or is at risk for developing a cardiac disorder.

The Bridging integrator 1 (BIN1) gene encodes several isoforms of a nucleocytoplasmic protein through alternative splicing. Ten BIN1 isoforms have been identified to date with two isoforms being ubiquitously expressed while others are present only in specific tissues. The BIN1 gene is located on chromosome 2 (2q14) between 127,805,599 and 127,864,903 bps (source: NCBI), and comprises 20 exons which can be alternatively spliced to form at least ten different isoforms. The BIN1 protein contains distinct domains such as a BAR domain (BIN1-amphiphysin-Rvs167), a phosphoinositide-binding domain, a clathrin-associated protein-binding domain (CLAP), a Myc-binding domain (MBD), and a Src homology 3 domain (SH3) (Prendergast G C, et al., *Biochim Biophys Acta.* 2009 1795(1):25-36). Exon 13 encodes a part of the CLAP domain.

As utilized herein, a 13+/17+ BIN1 polypeptide is a BIN1 isoform that comprises the polypeptide encoded by exon 13 of BIN1 (13+ BIN1 polypeptide) and the polypeptide encoded by exon 17 of BIN1 (17+ BIN1 polypeptide). Several BIN1 isoforms, including cardiac isoforms, comprise the 13+ BIN1 polypeptide and the 17+ BIN1 polypeptide. These include BIN1 isoform 1 (GenBank Accession No. NP_647593), BIN1 isoform 4 (GenBank Accession No. NP_647596), BIN1 isoform 5 (GenBank Accession No. NP_647597) and BIN1 isoform 6 (GenBank Accession No. NP_647598): Exon 13 and exon 17 of BIN1, are also known as exons 12a and exon 13, respectively. Therefore, it is understood that, the terms "exon 12a" and "exon 13" can be used interchangeably when referring to exon 13 of BIN1. Similarly, the terms "12a+ BIN1 polypeptide" and "13+ BIN1 polypeptide" can be used interchangeably when referring to a 13+ BIN1 polypeptide. It is also understood that the terms "exon 13" and "exon 17" can be used interchangeably when referring to exon 17 of BIN1. Similarly, the terms "13+ BIN1 polypeptide" and "17+ BIN1 polypeptide" can be used interchangeably when referring to a 17+ BIN1 polypeptide.

Exon 13, which encodes the 13+ BIN1 polypeptide of the 13+/17+ BIN1 polypeptide, can have the following nucleotide sequence: 5'-CTCCGGAAAG GCCCACCAGT CCCTCCGCCT CCCAAACACA CCCCGTCCAA GGAAGTCAAG CAGGAGCAGA TCCTCAGCCT GTTTGAGGAC ACGTTTGTCC CTGAGATCAG CGTGACCACC CCCTCCCAG-3' (SEQ ID NO: 1). Alternatively, the nucleotide sequence has at least 85, 90, or 95 percent identity to SEQ ID NO: 1 and such variations may or may not result in amino acid changes in the expressed protein. Optionally, exon 13 can encode an amino acid sequence comprising sequence LRKGPPVPPP PKHTPSKEVK QEQILSLFED TFVPEISVTT PSQ (SEQ ID NO: 2). Alternatively, the amino acid sequence can be at least 85, 90, or 95 percent identical to SEQ ID NO:2. Variations in the sequence can include amino acid insertions, deletions, or substitutions (including, for example, 1-5 conservative amino acid substitutions).

Exon 17, which encodes the 17+ BIN1 polypeptide of the 13+/17+ BIN1 polypeptide, can have the following nucleotide sequence: CCAGCAGAGGCCTCGGAGGTG-GCGGGTGGGACCCAACCTGCGGCTGGAGC CCAG-GAGCCAGGGGAGACGGCGGCAAGTGAAGCAGCC TCC (SEQ ID NO:3). Alternatively, the nucleotide sequence has at least 85, 90, or 95 percent identity to SEQ ID NO:3 and such variations may or may not result in amino acid changes in the expressed protein. Optionally, exon 17 can encode an amino acid sequence comprising sequence PAEASEVAGGTQPAAGAQEPGETAASEAAS (SEQ ID NO: 4). Alternatively, the amino acid sequence can be at least 85, 90, or 95 percent identical to SEQ ID NO: 4. Variations in the sequence can include amino acid insertions, deletions, or substitutions (including, for example, 1-5 conservative amino acid substitutions).

In the methods provided herein, a subject can be a vertebrate, and more specifically a mammal (e.g., a human, horse, pig, rabbit, dog, sheep, goat, non-human primate, cow, cat, guinea pig or rodent), a fish, a bird or a reptile or an amphibian. The term does not denote a particular age or sex. Thus, adult and newborn subjects, whether male or female, are intended to be covered. As used herein, patient or subject may be used interchangeably and can refer to a subject with or at risk of developing a cardiac disease or disorder. The term patient or subject includes human and veterinary subjects.

The subjects can optionally have one or more risk factors associated with a cardiac disorder. These include, but are not limited to, hypertension, obesity, depression, stress, diabetes, a diet high in saturated fat, family history, a genetic predisposition to a cardiac disorder, tobacco use and abnormal blood lipid levels (for example, high cholesterol, triglycerides, high low-density lipoproteins and/or low levels of high-density lipoproteins).

As used herein, control level refers to a level of 13+/17+ BIN1 expression from the same subject or a different subject or subjects. A level of 13+/17+ BIN1 expression from the same subject can be obtained at various time points previous to the most recent time point for comparison as to the levels of 13+/17+ BIN1 expression. A level of 13+/17+ BIN1 expression from a different subject can be obtained at the same time point as the present subject (e.g., the control subject and the present subject are the same age). Generally, the control subject and the present subject share many of the same or similar characteristics (e.g., age, weight, height, ethnicity, and breed).

A biological sample can be any sample obtained from an organism. Examples of biological samples include body fluids and tissue specimens. The source of the sample may be physiological media such as blood, serum, plasma, cerebral spinal fluid, breast milk, pus, tissue scrapings, washings, urine, feces, tissue, such as lymph nodes, spleen or the like. The term tissue refers to any tissue of the body, including blood, connective tissue, epithelium, contractile tissue, neural tissue, and the like.

A control level can be obtained from a control sample, which can comprise either a sample obtained from a control subject (e.g., from the same subject at a different time than the biological sample), or from a second subject, or can comprise a known standard.

Optionally, the control level can be normal, i.e. a level indicative of a subject that does not have a cardiac disorder or is not at greater risk, as compared to the general population, of developing a cardiac disorder. In such case, a detected level of 13+/17+ BIN1 polypeptide less than the control level indicates that the subject has a cardiac disorder or is at risk for developing a cardiac disorder, whereas, a detected level of 13+/17+ BIN1 polypeptide that is about the same as the control level or higher than the control level indicates that subject does not have a cardiac disorder and is not at risk for developing a cardiac disorder. Optionally, the control level is lower than normal, and a detected level of 13+/17+ BIN1 polypeptide comparable to or less than the control level indicates that the subject has a cardiac disorder or is at risk for developing a cardiac disorder. Optionally, the control level is higher than normal, and a detected level 13+17+ BIN1 polypeptide comparable to or higher than the control level indicates that the subject does not have a cardiac disorder and is not at risk for developing a cardiac disorder.

Control levels can be used to establish a threshold level, e.g., such that a 13+/17+ BIN1 polypeptide level less than the threshold value indicates the subject has or is at risk of developing a cardiac disorder. This threshold value can be determined empirically by comparing positive controls (samples from subjects with or at risk of developing a cardiac disorder) and negative controls (samples from subjects without a cardiac disorder, subjects successfully treated for a cardiac disorder or subjects that are not at greater risk for a cardiac disorder as compared to the general population). Such controls are optionally age matched or matched according to the type of cardiac disorder. In order to distinguish decreased 13+/17+ BIN1 polypeptide levels, the threshold value can be set at least 1, 1.5, 2, 2.5, 3, 3.5, 4, 4.5, or 5 standard deviations below the mean negative control value. Other statistical methods can be used to set a threshold value that is within the desired predictive power needed for the assay.

As used herein, a negative control level can be determined from a different subject(s) without a cardiac disorder, or the same subject(s) prior to the diagnosis of a cardiac disorder. Likewise, a positive control value can be determined from one or more subjects with or at risk of developing a cardiac disorder. Alternatively, the negative or positive control can be based on one or more samples containing known concentrations of 13+/17+ BIN1 polypeptide, such as recombinant 13+/17+ BIN1 polypeptide, as in a standard control.

Optionally, a 20% reduction in the level of 13+/17+ BIN1 polypeptide, as compared to the level of 13+/17+ BIN1 polypeptide in a sample previously obtained from the same subject, indicates that the subject has or is at risk for developing a cardiac disorder.

Optionally, a level of a 13+/17+ BIN1 polypeptide below a cutoff value indicates that the subject has or is at risk for developing a cardiac disorder. For example, a level of 13+/17+ BIN1 polypeptide from 0 to a cutoff value, for example, a cutoff value between about 0.25 ng/ml to about 1.0 ng/ml±20%, indicates that the subject has or is at risk of developing a cardiac disorder. Optionally, the cutoff value can be between about 0.25 ng/ml to about 1.0 ng/ml±10%. It is understood that the cutoff value can be any value including and in between about 0.25 ng/ml to about 1.0 ng/ml±20%. For example, if the cutoff value is 0.25 ng/ml, a 13+/17+ BIN1 polypeptide level less than or equal to 0.25 ng/ml indicates that the subject has or is at risk of developing a cardiac disorder and any value greater than 0.25 ng/ml indicates that the subject does not have or is not at risk for developing a cardiac disorder. In another example, if the cutoff value is 0.50 ng/ml, a 13+/17+ BIN1 polypeptide level less than or equal to 0.50 ng/ml indicates that the subject has or is at risk of developing a cardiac disorder and any value greater than 0.50 ng/ml indicates that the subject does not have or is not at risk for developing a cardiac disorder. In another example, if the cutoff value is 0.75 ng/ml, a 13+/17+ BIN1 polypeptide level less than or equal to 0.75 ng/ml indicates that the subject has or is at risk of developing a cardiac disorder and any value greater than 0.75 ng/ml indicates that the subject does not have or is not at risk for developing a cardiac disorder. In another example, if the cutoff value is 1.0 ng/ml, a 13+/17+ BIN1 polypeptide level less than or equal to 1.0 ng/ml indicates that the subject has or is at risk of developing a cardiac disorder and any value greater than 1.0 ng/ml indicates that the subject does not have or is not at risk for developing a cardiac disorder.

Optionally, a level of a 13+/17+ BIN1 polypeptide that is about 50% or less of the normal control level of 13+/17+ BIN1 polypeptide indicates that the subject has or is at risk for developing a cardiac disorder. Thus, about 50%, 45%, 40%, 35%, 30%, 25%, 20%, 15%, 10%, 5%, 1% of normal control levels indicate the subject has or is at risk of developing a cardiac disorder. A normal control value can be determined from the same subject prior to the onset of the risk or disease state or can be from cohorts which are optionally matched for age, sex, and other conditions or factors (e.g., post-surgical status, geographic location, etc.).

As utilized throughout, a cardiac disorder can be, but is not limited to, an arrhythmia (for example, ventricular arrhythmia), congestive heart failure, or cardiomyopathy.

Once a subject has been identified as having a cardiac disorder or being at risk of developing a cardiac disorder, further evaluation of the subject can be performed. Further evaluation can include an echocardiogram, a chest X-ray, an electrocardiogram (EKG), an exercise or perfusion stress test, cardiac catheterization, cardiac magnetic resonance imaging (MRI), a cardiac computed tomography (CT) scan, and/or Holter monitoring (continuous EKG). Measurement of increases in other blood-based cardiac biomarkers can also be performed. These biomarkers include, but are not limited to, troponin, B-type natriuretic polypeptide (BNP), C-reactive protein (CRP), and creatine phosphokinase (CK).

In the methods provided herein, the level of 13+/17+ BIN1 polypeptide in a biological sample can be determined by detecting a 13+/17+ BIN1 polypeptide, wherein the polypeptide comprises the polypeptide encoded by exon 13 of the BIN1 and the polypeptide encoded by exon 17 of BIN1. In order to detect the 13+/17+ BIN1 polypeptide in a biological sample, the biological sample is contacted with (i) an antibody that specifically binds to a polypeptide encoded by exon 13 of BIN1 (13+ BIN1 polypeptide) and (ii) an antibody that specifically binds to a polypeptide encoded by exon 17 of BIN1 (17+ BIN1 polypeptide) under conditions that allow identification of a 13+/17+ BIN1 polypeptide. It is understood that the methods provided herein are directed to identification of a BIN1 polypeptide comprising both a 13+ BIN1 polypeptide and 17+ BIN1 polypeptide, and not to identification of BIN1 polypeptides that comprise the 13+ BIN1 polypeptide and do not comprise the 17+ BIN1 polypeptide or to identification of BIN1 polypeptides that comprise the 17+ BIN1 polypeptide and do not comprise the 13+ BIN1 polypeptide.

As used herein, the term antibody encompasses, but is not limited to, whole immunoglobulin (i.e., an intact antibody) of any class. Chimeric antibodies and hybrid antibodies, with dual or multiple antigen or epitope specificities, and fragments, such as F(ab')2, Fab', Fab and the like, including hybrid fragments are useful herein. Thus, fragments of the antibodies that retain the ability to bind their specific antigens are provided and are useful in the methods taught here. For example, fragments of antibodies which maintain binding activity to a 13+ BIN1 polypeptide or a 17+ BIN1 polypeptide are included within the meaning of the term antibody or fragment thereof. Such antibodies and fragments can be made by techniques known in the art and can be screened for specificity and activity according to general methods for producing antibodies and screening antibodies for specificity and activity (See Harlow and Lane. Antibodies, A Laboratory Manual. Cold Spring Harbor Publications, New York (1988)). Also useful in the methods herein are conjugates of antibody fragments and antigen binding proteins (single chain antibodies) as described, for example, in U.S. Pat. No. 4,704,692, the contents of which are hereby incorporated by reference in their entirety.

Optionally, the antibody is a monoclonal antibody. The term monoclonal antibody as used herein refers to an antibody from a substantially homogeneous population of antibodies, i.e., the individual antibodies comprising the population are identical except for possible naturally occurring mutations that may be present in minor amounts. Monoclonal antibodies may be prepared using hybridoma methods, such as those described by Kohler and Milstein, Nature, 256:495 (1975) or Harlow and Lane, Antibodies, A Laboratory Manual. Cold Spring Harbor Publications, New York (1988). In a hybridoma method, a mouse or other appropriate host animal is typically immunized with an immunizing agent to elicit lymphocytes that produce or are capable of producing antibodies that will specifically bind to the immunizing agent.

The monoclonal antibodies can also be made by recombinant DNA methods, such as those described in U.S. Pat. No. 4,816,567. DNA encoding the monoclonal antibodies can be readily isolated and sequenced using conventional procedures (e.g., by using oligonucleotide probes that are capable of binding specifically to genes encoding the heavy and light chains of murine antibodies). The hybridoma cells can serve as a preferred source of such DNA. Once isolated, the DNA may be placed into expression vectors, which are then transfected into host cells, such as simian COS cells, Chinese hamster ovary (CHO) cells, plasmacytoma cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816,567) or by covalently joining to the immunoglobulin coding sequence all or part of the coding sequence for a non-immunoglobulin polypeptide.

In vitro methods are also suitable for preparing monovalent antibodies. Digestion antibodies to produce fragments thereof, particularly, Fab fragments, can be accomplished using routine techniques known in the art. For instance, digestion can be performed using papain. Examples of papain digestion are described in WO 94/29348, U.S. Pat. No. 4,342,566, and Harlow and Lane, Antibodies, A Laboratory Manual, Cold Spring Harbor Publications, New York, (1988). Papain digestion of antibodies typically produces two identical antigen binding fragments, called Fab fragments, each with a single antigen binding site, and a residual Fc fragment. Pepsin treatment yields a fragment, called the F(ab')2 fragment that has two antigen combining sites and is still capable of cross-linking antigen.

The Fab fragments produced in the antibody digestion can also contain the constant domains of the light chain and the first constant domain of the heavy chain. Fab' fragments differ from Fab fragments by the addition of a few residues at the carboxy terminus of the heavy chain domain including one or more cysteines from the antibody hinge region. The F(ab')2 fragment is a bivalent fragment comprising two Fab' fragments linked by a disulfide bridge at the hinge region. Fab'-SH is the designation herein for Fab' in Which the cysteine residue(s) of the constant domains bear a free thiol group.

Further provided herein is a humanized or human version of the antibody. Humanized and human antibodies can be made using methods known to a skilled artesian; for example, the human antibody can be produced using a germ-line mutant animal or by a phage display library.

An antibody that specifically binds to a BIN13+ polypeptide is provided herein. For example, an antibody that specifically binds to SEQ ID NO: 2, i.e. a polypeptide encoded by exon 13 of BIN1, can be used in the methods provided herein. The antibody can be a monoclonal antibody or a recombinant antibody. A monoclonal antibody (9D7 1C1) that specifically binds exon 13 can be used. 9D7 1C1 is described in International Application Publication No. WO/2013/049666 which is incorporated herein in its entirety by this reference. The complementarily determining regions (CDRs) of the 9D7 1C1 antibody's heavy chain comprises the amino acid sequences GFNIKDYY (SEQ ID NO:5), IDPENGNT (SEQ ID NO:6), and VRGEDYGG-YAMDY (SEQ ID NO:7). The CDRs of the 9D7 1C1 antibody's light chain comprise the amino acid sequences KSLLHSNGNTY (SEQ ID NO:8), MQHLEFPFT (SEQ ID NO:9) and QDVSTA (SEQ ID NO:10). Therefore, the disclosed monoclonal or recombinant antibody that selectively binds the 13+ BIN1 polypeptide comprises at least these CDRs, or CDRs having at least 95% to 99% identity with SEQ ID NO:5, SEQ ID NO:6, SEQ ID NO:7, SEQ ID NO:8, SEQ ID NO:9, and SEQ ID NO:10.

An antibody that specifically binds SEQ ID NO: 4, i.e. a polypeptide encoded by exon 17 of BIN1, can be used in the methods provided herein. The antibody can be a monoclonal antibody or a recombinant antibody. For example, the antibody can be a monoclonal antibody such as clone 99D, set forth in Catalog. No. #9428 from Sigma (St. Louis, Mo.).

As used herein, the phrase "specifically binds," or "selectively binds" refers to a binding reaction which is determinative of the presence of a polypeptide, for example a 13+ BIN1 polypeptide or a 17+ BIN1 polypeptide in a heterogeneous population of proteins, cells, proteoglycans, and other biologics. Thus, under designated conditions, the antibodies or fragments thereof of the present invention bind to a 13+ BIN1 polypeptide, a 17+ BIN1 polypeptide, or an epitope, fragment, or variant thereof and do not bind in a significant amount to other proteins or proteoglycans present in a biological sample as described herein.

Selective binding to an antibody under such conditions may require an antibody that is selected for its specificity for a 13+ BIN1 polypeptide, a 17+ BIN1 polypeptide, or a fragment thereof. A variety of immunoassay formats may be used to select antibodies that selectively bind with 13+ BIN1 polypeptide, a 17+ BIN1 polypeptide or a fragment thereof. For example, solid-phase ELISA immunoassays are routinely used to select antibodies selectively immunoreactive with a protein, proteoglycan, or variant, fragment, epitope, or protein core thereof. See Harlow and Lane. Antibodies, A Laboratory Manual. Cold Spring Harbor Publications, New York, (1988), for a description of immunoassay formats and conditions that could be used to determine selective binding. The binding affinity of a monoclonal antibody can, for example, be determined by the Scatchard analysis of Munson et al., Anal. Biochem., 107:220 (1980).

Preferably, in an ELISA, the binding of the antibody or fragments thereof of the present invention to a 13+ BIN1 polypeptide or a 17+ BIN1 polypeptide is at least 1.5 times the background level (i.e., comparable to non-specific binding or slightly above non-specific binding). More preferably, the binding of the antibody or fragments thereof of the present invention to 13+ BIN1 polypeptide or a 17+ BIN1 polypeptide is at least 2.5 times the background level.

Examples of analytical techniques useful in determining the expression of a polypeptide include immunohistochemistry, Western blot, enzyme-linked immunosorbent assay (ELISA), enzyme immunoassay (EIA), radioimmunoassay (RIA), protein array, or fluorescent activated cell sorting (FACS). These techniques are known by one of skill in the art. See, e.g., Sambrook et al., Molecular Cloning: A Laboratory Manual, $3^{rd}$ Ed., Cold Spring Harbor Press, Cold Spring Harbor, N.Y. (2001).

Optionally, the antibodies described herein can be labeled with a detectable moiety. For example, the detectable moiety can be selected from the group consisting of a fluorescent moiety, an enzyme-linked moiety (for example, a horseradish peroxidase conjugated antibody), a biotin moiety and a radiolabeled moiety.

As described in the Examples, the level of 13+/17+ BIN1 polypeptide in a biological sample can be detected using a capture ELISA assay. For example, a biological sample from the subject is contacted with an antibody that specifically binds to the 13+BIN1 polypeptide in order to capture all of the BIN1 isoforms in the biological sample that contain the 13+ BIN1, polypeptide, i.e., 13+ BIN1, isoforms. The captured 13+ BIN1 isoforms are then contacted with a detection antibody that specifically binds to the 17+ BIN1 polypeptide in order to identify 13+ BIN1 isoforms that also comprise a 17+ BIN1 polypeptide, i.e. 13+/17+ BIN1 isoforms or polypeptides. One of skill in the art would understand that the capture assay can also be performed by contacting the biological sample with an antibody that specifically binds to the 17+ BIN1 polypeptide in order to capture all of the BIN1 isoforms in the biological sample that contain the 17+ BIN1 polypeptide, i.e., 17+ BIN1 isoforms. The captured 17+ BIN1 isoforms are then contacted with a detection antibody that specifically binds to the 13+ BIN1 polypeptide in order to identify 17+ BIN1 isoforms that also comprise a 13+ BIN1 polypeptide, i.e., 13+/17+ BIN1 isoforms or polypeptides.

Further provided are methods of treating a subject with or at risk for a cardiac disorder. These methods comprise determining if a subject has a cardiac disorder or is at risk for developing a cardiac disorder according to the methods described herein, and treating the subject for the cardiac disorder.

As used herein the terms treatment, treat, or treating refers to a method of reducing the effects of a disease or condition or symptom of the disease or condition, Thus in the disclosed method, treatment can refer to a 10%, 20%, 30%, 40%, 50%, 60%, 70%, 80%, 90%, or 100% reduction in the severity of an established disease or condition or symptom of the disease or condition. Symptoms of cardiac disorders include, but are not limited to, chest pain, dizziness, shortness of breath and an abnormal heart rate. For example, a method for treating a disease is considered to be a treatment if there is a 10% reduction in one or more symptoms of the disease in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition.

Treatment will vary depending on several factors, including but not limited to, the type of cardiac disorder, age, body weight, general health, sex and diet of the subject. The mode and time of treatment will also vary depending on the severity of the disorder and can be determined by one of skill in the art.

For example, congestive heart failure can be treated by administering one or more of a diuretic (for example, furosemide, bumetanide or hydrocholorothiazide), an angiotensin converting enzyme (ACE) inhibitor, an angiotensin receptor blocker (ARB), a beta blocker, or an agent such as digoxin that can increase cardiac output. Treatment can be combined with a weight loss program, an exercise program, and/or cessation of smoking, as appropriate. Treatment for controlling high blood pressure, high cholesterol and diabetes can also be employed. Depending on the severity of heart failure, surgical procedures, for example, coronary artery bypass graft (CABG) surgery, valve surgery (for example, aortic valve replacement or mitral valve replacement), aneurysm repair, left ventricular assist device (LVAD) surgery, myomectomy, coronary reperfusion or a heart transplant can be performed.

Cardiomyopathy, a condition in which the chambers of the heart are enlarged and the heart becomes weak, can also be treated. As with other cardiac disorders, the treatment depends on the type of cardiomyopathy, the severity of symptoms, age and overall health, amongst other factors. For example, cardiomyopathy can be treated by administering an agent that lowers blood pressure, an agent that slows heart rate (for example, a beta blocker or a calcium channel blocker), an anti-arrhythmic agent, an anticoagulant or an anti-inflammatory agent, to name a few. A non-surgical procedure, such as alcohol septal ablation, can be performed. Surgical procedures such as open-heart surgery, implantation of a pacemaker or a heart transplant can also be performed to treat cardiomyopathy.

In another example, an arrhythmia can be treated by administering an agent that controls the heart rate of the subject, for example, a beta blocker. An anticoagulant, for example, warfarin, dabigatran or aspirin can also be administered. If medication is not able to control a persistent irregular heart rhythm, electrical cardioversion can be performed. A pacemaker or a cardioverter-defribillator (ICD) can also be implanted in the subject. In some cases, heart surgery may be necessary to correct heart disease caused by an arrhythmia. The methods provided herein can be used to determine if a subject that has had or is having ventricular arrhythmia is at risk for a future ventricular arrhythmia. For example, if a 20% reduction in the level of 13+/17+ BIN1 polypeptide, as compared to the level of 13+/17+ BIN1 polypeptide in a sample previously obtained from the same subject is observed, this indicates that the subject is at risk for a future ventricular arrhythmia and the subject should be treated accordingly. Early detection of a future ventricular arrhythmia can prompt earlier treatment of the subject and prevent serious consequences such as heart failure or death.

Further provided are methods of determining the efficacy of a therapy for a cardiac disorder in a subject. These comprise contacting a first biological sample from the subject with (i) an antibody that specifically binds to a polypeptide encoded by exon 13 of BIN1 and (ii) an antibody that specifically binds to a polypeptide encoded by exon 17 of BIN1, under conditions that allow identification of 13+17+ BIN1 polypeptides, to determine a first 13+17+ BIN1 level; obtaining a second biological sample from the subject after at least one treatment with a first therapy for the cardiac disorder; contacting the second biological sample with (i) the antibody that specifically binds to a polypeptide encoded by exon 13 of BIN1 and (ii) an antibody that specifically binds to a polypeptide encoded by exon 17 of BIN1, under conditions that allow identification of 13+17+ BIN1 polypeptides, to determine a second 13+17+ BIN1 level; comparing the first 13+17+ BIN1 polypeptide level with the second 13+17+ BIN1 polypeptide level; and selecting a second therapy for the cardiac disorder if the 13+17+ BIN1 polypeptide level decreases or fails to increase in the second biological sample as compared to the first biological sample, or continuing to treat the subject with the first therapy for the cardiac disorder if the 13+17+ BIN1 polypeptide level increases in the second biological sample as compared to the first biological sample. One of skill in the art can determine the proper dosages or change in treatment regimens.

Also provided are methods of determining the progression of a cardiac disorder or an increase in the risk of developing a cardiac disorder in a subject. These methods comprise obtaining a first biological sample from the subject; determining a first 13+17+ BIN1 polypeptide level in the first biological sample by contacting the sample with (i) an antibody that specifically binds to a 13+ BIN1 polypeptide and (ii) an antibody that specifically binds to a 17+ BIN1 polypeptide; obtaining a second biological sample from the subject; detecting a second 13+17+ BIN1 polypeptide level in the second biological sample by contacting the sample with (i) an antibody that specifically binds to a 13+ BIN1 polypeptide and (ii) an antibody that specifically binds to a 17+ BIN1 polypeptide; comparing the first 13+17+ BIN1 polypeptide level with the second 13+17+ BIN1 polypeptide level, wherein, if the 13+17+ BIN1 polypeptide level decreases in the second biological sample as compared to the first biological sample, the cardiac disorder in the subject has progressed or the risk of developing a cardiac disorder has increased in the subject.

Progression of a cardiac disorder or an increase in the risk of developing a cardiac disorder generally indicates the need for additional testing, a change in treatment and/or a change in frequency of treatment. One of skill in the art can determine what changes in treatment are necessary to treat a subject with a cardiac disorder that has progressed or a subject whose risk of developing a cardiac disorder has increased. A similar level of 13+/17+ BIN1 expression as compared to a previous biological sample indicates that the cardiac disorder has not progressed, while a higher level of 13+/17+ BIN1 expression as compared to a previous biological sample indicates improvement. Generally, such an improvement indicates the success of the treatment. In such case, the treatment can be continued or even discontinued if the level of 13+/BIN17+ polypeptide is sufficiently high.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including in the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

EXAMPLES

Antibodies

To measure the level of BIN1 cardiac isoform 13+/17+ BIN1 (also known as 12a+/13+ BIN1) in blood samples, two BIN1 antibodies were used in enzyme-linked immunosorbent assay (ELISA). The detection of 13+/17+ BIN1 cardiac isoform was performed using a mouse monoclonal anti-BIN1 exon 17 antibody (clone 99D, Sigma, Catalog. No. #9428, St. Louis, Mo.), as a capture antibody. The detection of the subset of BIN1 13+/17+ isoform that contains the polypeptide encoded by exon 17 was performed using a horse radish peroxidase (HRP)-conjugated mouse monoclonal anti-BIN1 exon 13 (recombinant antibody clone #9D71C1).

Detection of Plasma BIN1 Protein by Capture Sandwich ELISA

Antibody combinations used in the ELISA assays are described above. Round bottom 96-well plates were coated at 4° C. overnight with the capture antibody (5 µg/ml) diluted in 0.1M sodium carbonate buffer, at pH 9.0. The plates were washed three times with Tris-buffered saline TWEEN-20 (TBST) to remove unbound antibody and blocked for 1 hour at room temperature with 1% bovine serum albumin (BSA) in TEST (blocking buffer) on an orbital shaker. 50 µl of standards (purified recombinant BIN1 proteins) and each plasma sample was added, in duplicate, and plates were incubated overnight at 4° C. with orbital rotation. The samples were then aspirated and plates were washed twice quickly and three times for 5 minutes with TBST. Primary detection antibody (50 µl HRP-conjugated mouse anti BIN1 exon 13, 5 µg/ml in blocking buffer) was then added and the plates were incubated for 1 hour at room temperature with orbital rotation. The detection antibody was then aspirated and the plates were washed twice quickly, followed by three times for 5 minutes with TBST. Tetramethylbenzidine (FMB) substrate was added and the plates were incubated in the dark room for 30 minutes before reaction termination with 1 N hydrochloric acid. Following the reaction termination, the plates were read using an ELx800 microplate spectrophotometer (BIOTEK, Winooski, Vt.) and optical density (OD) values were determined at 405 nm. A standard curve was generated from the OD values of the protein standards of known protein concentration. BIN1 concentrations of each sample were then derived from the standard curve.

Dog Samples

Eight blood samples from apparently healthy dogs (referred to as normal) and ten blood samples from dogs with cardiomyopathy (referred to as CM) were collected for this study. 10 ml of whole blood was obtained in EDTA anticoagulated tubes. The samples were centrifuged at 4° C. at 4,000 rpm for 20 minutes to separate plasma from the blood cells. Plasma was then collected and aliquoted into 200 to 500 µl it aliquots and snap frozen in liquid nitrogen followed by storage in a −80° C. freezer for later analysis. On the day of the ELISA experiments, the samples were thawed on ice and centrifuged again at 4° C., at 4,000 rpm, to remove any precipitants.

Results

Standard Curves

Figure 1:
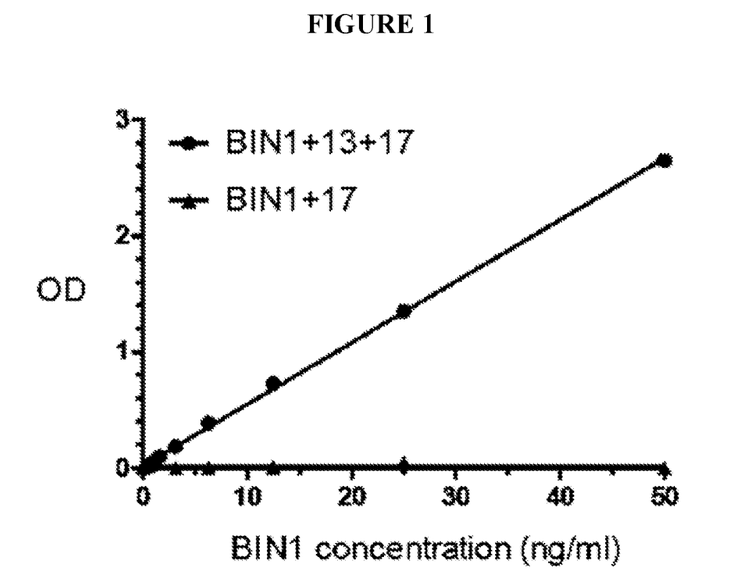
FIG. 1 is a graph showing that, when using a combination of a capture antibody (anti-BIN1 exon 17 antibody) and a detection antibody (anti-BIN1 exon 13 antibody), there is a linear correlation between 13+/17+ BIN1 polypeptide level and optical density (OD) signal ($R^2=0.99$).

In this study, purified recombinant BIN1 protein isoforms 13+/17+ BIN1 and 17+ BIN1 were used as positive and negative controls, respectively. GST-tagged BIN1 recombinant protein (13+/17+ BIN1 and 17+ BIN1) were overexpressed in human HEK-293 cells. The total cellular protein lysate was collected from these cells, and glutathione beads were then used to purify BIN1 protein. The BIN1 protein that attaches to glutathione beads was then eluted in imidazole buffer. Using the specific cardiac BIN1 test, using a combination of capture with anti-BIN1 exon 17 antibody and detection with anti-BIN1 exon 13 antibody, as shown in FIG. 1, only 13+/17+ BIN1, but not 17+ BIN1, develops a dose dependent increase of OD signal. Within the range of 0-50 ng of purified 13+/17+ BIN1, there is a linear correlation between 13+/17+ BIN1 protein level and OD signal ($R^2=0.99$).

Dog Samples

Figure 2:
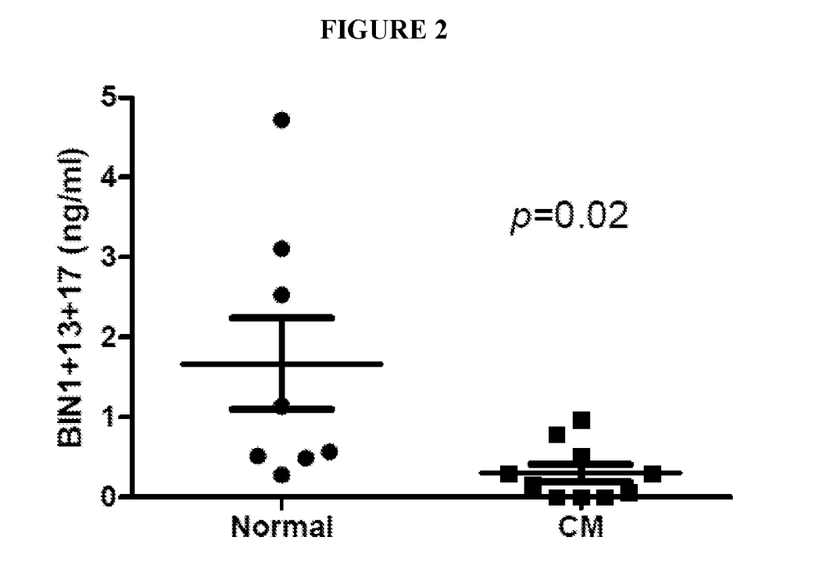
FIG. 2 shows that the plasma level of cardiac of the 13+/17+ BIN1 cardiac isoform in normal dog samples is 1.67±0.57 ng/ml (mean±SEM) with a median value of 0.86. However, in cardiomyopathy dogs, plasma 13+/17+ BIN1 polypeptide level is significantly reduced to 0.30±0.11 ng/ml (mean±SEM, median at 0.22, p=0.02).
Figure 3:
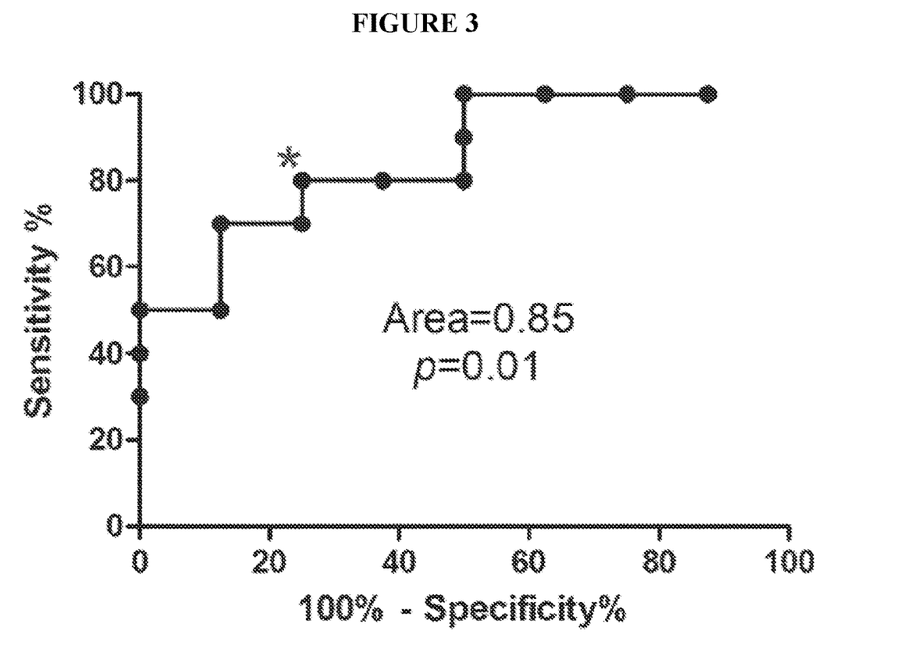
FIG. 3 is a graph showing a receiver operating characteristic (ROC) curve generated by plotting the true positive rate (Sensitivity %, Y-axis) against the false positive rate (100%-Specificity %, X-axis) at various threshold settings of plasma level of 13+/17+ BIN1 polypeptide. The area under the ROC curve is 0.85 (p=0.01), indicating that plasma 13+/17+ BIN1 polypeptide is useful for detecting cardiomyopathy.

A BIN1 cardiac test was used to analyze 18 dog samples (8 normal and 10 with cardiomyopathy) to detect the levels of cardiac BIN1 isoform in normal versus cardiomyopathy (CM) dogs. As indicated in FIG. 2, the plasma level of cardiac 13+/17+ BIN1 isoform in normal dog samples is 1.67±0.57 ng/ml (mean±SEM) with a median value of 0.86. In cardiomyopathy dogs, plasma 13+/17+ BIN1 is significantly reduced to 0.30±0.11 ng/ml (mean±SEM, median at 0.22, p=0.02). Next, a receiver operating characteristic (ROC) curve was generated by plotting the true positive rate (Sensitivity %, Y-axis) against the false positive rate (100%-Specificity %, X-axis) at various threshold settings of plasma level of 13+/17+ BIN1. As indicated in FIG. 3, the area under the ROC curve is 0.85 (p=0.01) indicates that plasma 13+/17+ BIN1 polypeptide is useful for detecting cardiomyopathy. For example, at plasma 13+/17+ BIN1 polypeptide level <0.39 ng/ml (star marked point in FIG. 3), 70% (true positive rate) of cardiomyopathy patients can be detected with only a 12% false positive rate.

Diagnosing Heart Failure

In order to diagnose heart failure in a subject, a BIN1 cardiac test is performed on a patient presenting with one or more symptoms of heart failure. Symptoms include, but are not limited to, fatigue, shortness of breath, exercise intolerance, weight gain due to fluid retention, swelling in the extremities, difficulty lying flat due to trouble breathing, non-specific pain, loss of appetite or constipation. A sample, for example, plasma, is obtained from the subject and the level of cardiac 13+/17+ BIN1 isoform is determined. If the level of cardiac 13+/17+ BIN1 isoform is low, for example, below a cutoff value between about 0.25 ng/ml and about 1.0 ng/ml±20% or the level is about 50% or less of normal control, an echocardiogram is ordered to evaluate heart function. If the echocardiogram reveals that the patient has heart failure due to reduced ejection fraction (HFrEF), treatment of the subject is initiated. Treatment can include, for example, administration of one or more beta blockers, one or more ACE inhibitors, one or more angiotensin-receptor blockers, and/or one or more diuretics. If the echocardiogram reveals that the patient has heart failure due to preserved ejection fraction (HFpEF), i.e., normal ejection fraction, yet restricted filling and volume overload, treatment of the subject is initiated. Treatment can include, for example, administration of one or more beta blockers, one or more ACE inhibitors, one or more angiotensin-receptor blockers, and/or one or more diuretics. The subject diagnosed with heart failure due to HFpEF should also be tested for ischemic heart disease. If the echocardiogram reveals that the patient has heart failure due to valvular heart disease, treatment of the subject is initiated. Treatment can include, for example, administration of one or more beta blockers, one or more ace-inhibitors, one or more angiotensin-receptor blockers, and/or one or more diuretics. The patient can also be evaluated for surgical repair or replacement of the defective heart valve.

For patients with known heart failure, the level of cardiac 13+/17+ BIN1 isoform can be determined every three to six months and an echocardiogram ordered when the level decreases as compared to a level of cardiac 13+/17+ BIN1 isoform detected previously in the subject or falls below a cutoff value, for example, below a cutoff value between about 0.25 ng/ml±20% and about 1.0 ng/ml±20% or when the level is about 50% or less of normal level of cardiac 13+/17+ BIN1 isoform.

Tracking Disease Progression

A patient with chronic hypertension, but with a normal functioning hypertensive heart, can have the level of cardiac 13+/17+ BIN1 isoform determined annually if the patient is asymptomatic or each time the patient has one or more symptoms related to heart failure. When the level of cardiac 13+/17+ BIN1 isoform decreases below a cutoff level, for example, below a cutoff value between about 0.25 ng/ml and about 1.0 ng/ml±20% or the level of cardiac 13+/17+ BIN1 isoform is about 50% or less of normal, the patient should be evaluated for HFpEF, for example, by echocardiogram. Once a decreased level of cardiac 13+/17+ BIN1 isoform is detected, the patient can be treated by administering one or more beta blockers, one or more ACE inhibitors, one or more angiotensin-receptor blockers, and/or one or more diuretics.

A patient with diabetes, but with a normal functioning heart, can have the level of cardiac 13+/17+ BIN1 isoform determined annually if the patient is asymptomatic or each time the patient has one or more symptoms related to heart failure. When the level of cardiac 13+/17+ BIN1 isoform decreases below a cutoff level, for example, below a cutoff value between about 0.25 ng/ml and about 1.0 ng/ml±20% or the level of cardiac 13+/17+ BIN1 isoform is about 50% or less of normal control, the patient should be evaluated for HFpEF, for example, by echocardiogram. Once a decreased level of cardiac 13+/17+ BIN1 isoform is detected, the patient can be treated by administering one or more beta blockers, one or more ACE inhibitors, one or more angiotensin-receptor blockers, and/or one or more diuretics.

A patient with normal functioning ischemic heart disease can have the level of cardiac 13+/17+ BIN1 isoform determined annually if the patient is asymptomatic or each time the patient has one or more symptoms related to heart failure. When the level of cardiac 13+/17+ BIN1 isoform decreases below a cutoff level, for example, below a cutoff value between about 0.25 ng/ml and about 1.0 ng/ml±20% or the level is at or below about 50% or less of normal control, the patient should be evaluated for HFpEF, for example, by being referred to a cardiologist and/or having an echocardiogram performed. Once a decreased level of cardiac 13+/17+ BIN1 isoform is detected, the patient can also be treated by administering one or more beta blockers, one or more ACE inhibitors, one or more angiotensin-receptor blockers, and/or one or more diuretics. This patient should also be assessed for ischemic heart disease by stress test or cardiac catheterization.

A patient with known valvular heart disease can have the level of cardiac 13+/17+ BIN1 isoform determined every six to twelve months if the patient is asymptomatic or each time the patient has one or more symptoms related to heart failure. When the level of cardiac 13+/17+ BIN1 isoform decreases below a cutoff level, for example, below a cutoff value between about 0.25 ng/ml and about 1.0 ng/ml±20% or the level is about 50% or less of normal, this is indicative of worsening heart function associated with valvular heart disease, such as aortic stenosis or mitral valve regurgitation. The patient should be assessed for surgical intervention.

Post-Surgical Recovery of Heart Function

After heart surgery, for example, after aortic valve replacement, mitral valve replacement, myomectomy or coronary reperfusion, heart transplantation, a patient can be monitored for recovery of heart function by determining the level of cardiac 13+/17+ BIN1 isoform in the patient. If the level of cardiac 13+/17+ BIN1 isoform does not improve as compared to the level of cardiac 13+/17+ BIN1 isoform prior to surgery or improves and then decreases, the patient should be reevaluated for additional procedures or revision of the original surgery.

What is claimed is:

1. A method for determining if a subject has a cardiac disorder or is at risk for developing a cardiac disorder:
   (a) contacting a plasma sample from the subject with (i) an antibody that specifically binds to a polypeptide encoded by exon 13 of BIN1 (13+ BIN1 polypeptide) and (ii) an antibody that specifically binds to a polypeptide encoded by exon 17 of BIN1 (17+ BIN1 polypeptide) under conditions that allow identification of a 13+/17+ BIN1 polypeptide, wherein the 13+/17+ BIN1 polypeptide comprises the polypeptide encoded by exon 13 and the polypeptide encoded by exon 17; and
   (b) determining a total level of 13+/17+ BIN1 polypeptide, wherein a decrease in the total BIN1 polypeptide level as compared to a control level indicates that the subject has a cardiac disorder or is at risk for developing a cardiac disorder.

2. The method of claim 1, wherein the cardiac disorder is arrhythmia, cardiomyopathy, or congestive heart failure.

3. The method of claim 1, wherein the subject is an individual with one or more risk factors associated with a cardiac disorder.

4. The method of claim 1, wherein the antibody that specifically binds to the 13+ BIN1 polypeptide, specifically binds to SEQ ID NO: 2.

5. The method of claim 4, wherein the antibody is a monoclonal antibody or a recombinant antibody.

6. The method of claim 4, wherein the complementarity determining regions (CDRs) of the antibody heavy chain comprise the amino acid sequences SEQ ID NO: 5, SEQ ID NO: 6, and SEQ ID NO: 7; and/or the complementarity determining regions (CDRs) of the antibody light chain comprise the amino acid sequences SEQ ID NO: 8, SEQ ID NO: 9, and SEQ ID NO: 10.

7. A method of treating a subject with or at risk for a cardiac disorder comprising:
  (a) determining if a subject has a cardiac disorder or is at risk for developing a cardiac disorder according to the method of claim 1; and
  (b) treating the subject for the cardiac disorder.

8. A method of determining the efficacy of a therapy for a cardiac disorder in a subject comprising:
  (a) contacting a first plasma sample from the subject with (i) an antibody that specifically binds to a polypeptide encoded by exon 13 of BIN1 and (ii) an antibody that specifically binds to a polypeptide encoded by exon 17 of BIN1, under conditions that allow identification of 13+17+ BIN1 polypeptides, to determine a first 13+17+ BIN1 level;
  (b) obtaining a second plasma sample from the subject after at least one treatment with a first therapy for the cardiac disorder;
  (c) contacting the second plasma sample with (i) the antibody that specifically binds to a polypeptide encoded by exon 13 of BIN1 and (ii) an antibody that specifically binds to a polypeptide encoded by exon 17 of BIN1, under conditions that allow identification of 13+17+ BIN1 polypeptides, to determine a second 13+17+ BIN1 level;
  (d) comparing the first 13+17+ BIN1 polypeptide level with the second 13+17+ BIN1 polypeptide level; and
  (e) selecting a second therapy for the cardiac disorder if the 13+17+ BIN1 polypeptide level decreases or fails to increase in the second plasma sample as compared to the first plasma sample, or continuing to treat the subject with the first therapy for the cardiac disorder if the 13+17+ BIN1 polypeptide level increases in the second plasma sample as compared to the first plasma sample.

9. The method of claim 8, wherein the cardiac disorder is arrhythmia, cardiomyopathy, or congestive heart failure.

10. The method of claim 8, wherein the antibody that specifically binds to the 13+ BIN1 polypeptide, specifically binds to SEQ ID NO: 2.

11. The method of claim 10, wherein the antibody is a monoclonal antibody or a recombinant antibody.

12. The method of claim 10, wherein the complementarity determining regions (CDRs) of the antibody heavy chain comprise the amino acid sequences SEQ ID NO: 5, SEQ ID NO: 6, and SEQ ID NO: 7; and/or the complementarity determining regions (CDRs) of the antibody light chain comprise the amino acid sequences SEQ ID NO: 8, SEQ ID NO: 9, and SEQ ID NO: 10.

13. A method of determining the progression of a cardiac disorder or an increase in the risk of developing a cardiac disorder in a subject comprising:
  (a) obtaining a first plasma sample from the subject;
  (b) determining a first 13+17+ BIN1 polypeptide level in the first plasma sample by contacting the sample with (i) an antibody that specifically binds to a 13+ BIN1 polypeptide and (ii) an antibody that specifically binds to a 17+ BIN1 polypeptide;
  (c) obtaining a second plasma sample from the subject;
  (d) detecting a second 13+17+ BIN1 polypeptide level in the second plasma sample by contacting the sample with (i) an antibody that specifically binds to a 13+ BIN1 polypeptide and (ii) an antibody that specifically binds to a 17+ BIN1 polypeptide;
  (e) comparing the first 13+17+ BIN1 polypeptide level with the second 13+17+ BIN1 polypeptide level, wherein, if the 13+17+ BIN1 polypeptide level decreases in the second plasma sample as compared to the first plasma sample, the cardiac disorder in the subject has progressed or the risk of developing a cardiac disorder has increased in the subject.

14. The method of claim 13, wherein the cardiac disorder is arrhythmia, cardiomyopathy, or congestive heart failure.

15. The method of claim 13, wherein the antibody that specifically binds to the 13+ BIN1 polypeptide, specifically binds to SEQ ID NO: 2.

16. The method of claim 15, wherein the antibody is a monoclonal antibody or a recombinant antibody.

17. The method of claim 15, wherein the complementarity determining regions (CDRs) of the antibody heavy chain comprise the amino acid sequences SEQ ID NO: 5, SEQ ID NO: 6, and SEQ ID NO: 7; and/or the complementarity determining regions (CDRs) of the antibody light chain comprise the amino acid sequences SEQ ID NO: 8, SEQ ID NO: 9, and SEQ ID NO: 10.

18. The method of claim 13, further comprising treating the subject for the cardiac disorder or initiating or modifying treatment of the subject if the subject's cardiac disorder has progressed or is at risk of progressing.

* * * * *

SEQUENCE LISTING

<160> NUMBER OF SEQ ID NOS: 10

<210> SEQ ID NO 1
<211> LENGTH: 129
<212> TYPE: DNA
<213> ORGANISM: Homo sapiens

<400> SEQUENCE: 1
ctccggaaag gcccaccagt ccctccgcct cccaaacaca ccccgtccaa ggaagtcaag    60
caggagcaga tcctcagcct gtttgaggac acgtttgtcc ctgagatcag cgtgaccacc   120
ccctcccag                                                          129

<210> SEQ ID NO 2
<211> LENGTH: 43
<212> TYPE: PRT
<213> ORGANISM: Homo sapiens

<400> SEQUENCE: 2

Leu Arg Lys Gly Pro Pro Val Pro Pro Pro Lys His Thr Pro Ser
1               5                   10                  15

Lys Glu Val Lys Gln Glu Gln Ile Leu Ser Leu Phe Glu Asp Thr Phe
            20                  25                  30

Val Pro Glu Ile Ser Val Thr Thr Pro Ser Gln
        35                  40

<210> SEQ ID NO 3
<211> LENGTH: 90
<212> TYPE: DNA
<213> ORGANISM: Homo sapiens

<400> SEQUENCE: 3
ccagcagagg cctcggaggt ggcgggtggg acccaacctg cggctggagc ccaggagcca    60
ggggagacgg cggcaagtga agcagcctcc                                    90

<210> SEQ ID NO 4
<211> LENGTH: 30
<212> TYPE: PRT
<213> ORGANISM: Homo sapiens

<400> SEQUENCE: 4

Pro Ala Glu Ala Ser Glu Val Ala Gly Gly Thr Gln Pro Ala Ala Gly
1               5                   10                  15

Ala Gln Glu Pro Gly Glu Thr Ala Ala Ser Glu Ala Ala Ser
            20                  25                  30

<210> SEQ ID NO 5
<211> LENGTH: 8
<212> TYPE: PRT
<213> ORGANISM: Artificial sequence
<220> FEATURE:
<223> OTHER INFORMATION: Synthetic construct

<400> SEQUENCE: 5

Gly Phe Asn Ile Lys Asp Tyr Tyr
1               5

<210> SEQ ID NO 6
<211> LENGTH: 8
<212> TYPE: PRT
<213> ORGANISM: Artificial sequence
<220> FEATURE:
<223> OTHER INFORMATION: Synthetic construct

```
<400> SEQUENCE: 6

Ile Asp Pro Glu Asn Gly Asn Thr
1               5

<210> SEQ ID NO 7
<211> LENGTH: 13
<212> TYPE: PRT
<213> ORGANISM: Artificial sequence
<220> FEATURE:
<223> OTHER INFORMATION: Synthetic construct

<400> SEQUENCE: 7

Val Arg Gly Glu Asp Tyr Gly Gly Tyr Ala Met Asp Tyr
1               5                   10

<210> SEQ ID NO 8
<211> LENGTH: 11
<212> TYPE: PRT
<213> ORGANISM: Artificial sequence
<220> FEATURE:
<223> OTHER INFORMATION: Synthetic construct

<400> SEQUENCE: 8

Lys Ser Leu Leu His Ser Asn Gly Asn Thr Tyr
1               5                   10

<210> SEQ ID NO 9
<211> LENGTH: 9
<212> TYPE: PRT
<213> ORGANISM: Artificial sequence
<220> FEATURE:
<223> OTHER INFORMATION: Synthetic construct

<400> SEQUENCE: 9

Met Gln His Leu Glu Phe Pro Phe Thr
1               5

<210> SEQ ID NO 10
<211> LENGTH: 6
<212> TYPE: PRT
<213> ORGANISM: Artificial sequence
<220> FEATURE:
<223> OTHER INFORMATION: Synthetic construct

<400> SEQUENCE: 10

Gln Asp Val Ser Thr Ala
1               5
```